United States Patent
Lin et al.

(10) Patent No.: US 6,838,541 B2
(45) Date of Patent: Jan. 4, 2005

(54) METHOD OF MAKING SILOXANE-BASED POLYAMIDE ELASTOMERS

(75) Inventors: Zuchen Lin, Midland, MI (US); Kimmai Thi Nguyen, Midland, MI (US); Lenin James Petroff, Bay City, MI (US)

(73) Assignee: Dow Corning Corporation, Midland, MI (US)

( * ) Notice: Subject to any disclaimer, the term of this patent is extended or adjusted under 35 U.S.C. 154(b) by 98 days.

(21) Appl. No.: 10/365,851

(22) Filed: Feb. 12, 2003

(65) Prior Publication Data

US 2004/0156807 A1 Aug. 12, 2004

(51) Int. Cl.⁷ .............................................. C08G 77/08
(52) U.S. Cl. .............................. 528/28; 528/15; 528/31
(58) Field of Search ....................................... 528/15, 26

(56) References Cited

U.S. PATENT DOCUMENTS

| | | | |
|---|---|---|---|
| 4,675,372 A | * 6/1987 | Policastro | 528/26 |
| 5,136,068 A | 8/1992 | Bahr et al. | 556/445 |
| 5,500,209 A | 3/1996 | Ross et al. | 424/66 |
| 5,603,925 A | 2/1997 | Ross et al. | 424/65 |
| 5,811,487 A | 9/1998 | Schulz, Jr. et al. | 524/862 |
| 5,889,108 A | 3/1999 | Zhang | 524/862 |
| 5,919,441 A | 7/1999 | Mendolia et al. | 424/78.08 |
| 5,981,680 A | * 11/1999 | Petroff et al. | 528/26 |
| 6,051,216 A | 4/2000 | Barr et al. | 424/78.35 |
| 6,353,076 B1 | 3/2002 | Barr et al. | 528/28 |
| 6,451,295 B1 | 9/2002 | Cai et al. | 424/65 |

* cited by examiner

Primary Examiner—Margaret G. Moore
(74) Attorney, Agent, or Firm—Alan Zonbeck

(57) ABSTRACT

Siloxane-based polyamide elastomers can be prepared by heating a reaction mixture containing an olefinic acid and an organic amine to form an organic amide, and reacting the organic amide with a hydride functional polyorganosiloxane in the presence of a hydrosilylation catalyst to form the siloxane-based polyamide elastomer. The hydride functional polyorganosiloxane contains at least one pendant hydrogen. The elastomers are useful additives in personal care products and can be applied to the hair, the skin, or the underarm. They can also be used to modify thermoplastic nylons, and for treating woven and non-woven textiles, such as air bags, carpeting, and apparel.

16 Claims, No Drawings

METHOD OF MAKING SILOXANE-BASED POLYAMIDE ELASTOMERS

FIELD OF THE INVENTION

This invention is an improvement and a modification of the method of making siloxane-based polyamides, as generally described in U.S. Pat. No. 5,981,680 (Nov. 9, 1999), referred to hereafter as the '680 patent. The '680 patent is assigned to the same assignee as the present invention. The improvement and modification according to the present invention relates to enablement of the process of the '680 patent for the production of siloxane-based polyamides which are elastomers.

BACKGROUND OF THE INVENTION

Elastomers differ from linear polymers because of crosslinking. The term crosslinking refers to connections between linear polymers. The reactive chemical that creates the connections between linear polymers is called a crosslinker. Many silicone elastomers are made from linear silicone polymers that contain reactive sites along their polymer chain. These reactive sites react with the crosslinker to form connections between the linear polymer chains.

The creation of connections, i.e., crosslinks, between the linear polymers converts linear polymers such as polydimethylsiloxane fluids into silicone elastomers. Elastomers have very different physical and chemical properties from linear polymers, and the properties of an elastomer depends very much on the number of crosslinks. Thus, an elastomer with a relatively small number of crosslinks will generally be very soft, and will swell significantly in the presence of a compatible solvent(s). As the number of crosslinks increase, however, the hardness of the elastomer increases, with the result that the elastomer swells to a lesser extent in the presence of solvents. A term often used to describe the number of crosslinks in an elastomer is crosslink density. Crosslink density refers to the number of crosslinks for a given length of the linear polymer.

Unlike linear polymers, it is nearly impossible to determine molecular weight for elastomers, because they are in effect one gigantic polymer with no definite beginning or end. Elastomers generally will not flow, and so one cannot measure a viscosity for such materials. In fact, the term elastomer is derived from the same root word as elastic, a reference to the phenomenon that such materials snap back when a force is applied and then released.

Silicone elastomers can be produced from linear silicone polymers by a wide variety of crosslinking reactions. In the case of a silicone bathtub caulk, for example, the crosslinking reaction occurs between reactive silanol groups ($\equiv$SiOH) and acetoxy groups ($\equiv$SiOCOCH$_3$). For each crosslink formed, a molecule of acetic acid is released, which produces the characteristic vinegar smell as the caulk cures. The acetoxy group in such a scenario is called a leaving group, because it is converted to acetic acid which leaves, i.e., evaporates, when the crosslink is formed. While there exist many other different crosslinking schemes to prepare silicone elastomers, those silicone elastomers designed for use in personal care applications all typically use the same basic reaction, i.e., hydosilylation. Hydrosilylation is a reaction in which a vinyl group reacts with a silicon hydride in the presence of a platinum catalyst as shown below:

$\equiv$Si H+CH$_2$=CH—R→$\equiv$Si—CH$_2$—CH$_2$—R

Pt Catalyst

There are many advantages for using hydrosilylation as the crosslinking reaction. It proceeds very rapidly, it requires very small amounts of a platinum catalyst, i.e., typically Karstedt's catalyst, as known in the art, and it does not involve a leaving group. But the most important reason for its popularity is that there are very few limitations in the types of materials that can be used as crosslinkers and polymers in the preparation of silicone elastomers. For example, the SiH functionality can be part of a polyorganosiloxane polymer, a silicone resin, or some other type of silicone or organosilicon composition. Similarly, the R group can be attached to a silicone, a hydrocarbon, or some other type of organic compound. This flexibility allows one skilled in the art to graft many and varied types of functional groups into the elastomer.

While siloxane-based polyamide elastomers are generally known in the art, as evidenced by U.S. Pat. No. 4,675,372 (Jun. 23, 1987), referred to hereafter as the '372 patent, it does not employ hydrosilylation as the mechanism of reaction, and the components used to form siloxane-based polyamide elastomers in the '372 patent are not the same as, or the equivalent of, the components according to the present invention. Hence, the elastomers prepared according to the '372 patent would necessarily not be the same as the elastomers prepared herein.

While the '680 patent does refer to a method of preparing crosslinked molecules, it differs from the method herein in that the '680 patent uses a triamine, i.e., a trifunctioanl amine, in place of an organic diamine, in the preparation of the vinyl functional amide and the hydride functional polyorganosiloxane in the '680 patent is $\equiv$SiH endblocked and contains no pendant hydrogen, as in the method of this invention. These differences are significant in that when an organic vinyl functional triamide is used, the crosslinker is the hydride functional polyorganosiloxane rather than the organic amide, i.e., see Formula IV in the '680 patent. In the method according to this invention, however, the organic diamide is the crosslinker between molecular chains of the pendant hydrogen containing hydride functional polyorganosiloxane. Hence, elastomers prepared according to the '680 patent would necessarily not be the same as the elastomers prepared herein.

SUMMARY OF THE INVENTION

This invention is directed to a method of making a siloxane-based polyamide elastomer by reacting an organic amide with a hydride functional polyorganosiloxane in the presence of a hydrosilylation catalyst to form the siloxane-based polyamide elastomer. The hydride functional polyorganosiloxane is a polymer or copolymer containing at least one pendant hydrogen.

The organic amine can be a compound such as hexamethylene diamine, ethylene diamine, and decamethylene diamine. The olefinic acid can be a compound such as undecylenic acid, acrylic acid, 3-butenoic acid, and 4-pentenoic acid.

If desired, a specified amount of a chain stopping agent can be included. Suitable chain stopping agents are described in our copending U.S. patent application Ser. No. 10/145,311, filed on May 15, 2002, and entitled *Methods for Making Silicone-Organic Copolymers*, which application is assigned to the same assignee as the present invention The siloxane-based polyamide elastomer prepared by this method is a useful component of personal care type products, and it can be applied to the hair, skin, or underarm areas of the human body. It can also be used to modify thermoplastic nylons, and for treating woven and nonwoven textiles, such as air bags, carpeting, and apparel.

These and other features of the invention will become apparent from a consideration of the detailed description.

DETAILED DESCRIPTION OF THE INVENTION

The Hydride Functional Polyorganosiloxane

The hydride functional polyorganosiloxane (HFPOS) which is used in the process of the present invention is a HYPOS conforming generally to a polymer or copolymer having a formula corresponding to one of Formulas I–IV shown below.

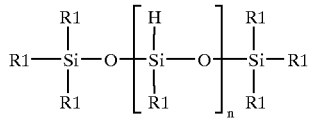

Formula I

The Olefinic Acid

Some representative examples of suitable olefinic acids which can be used include undecylenic acid $H_2C=CH(CH_2)_8COOH$, acrylic acid $H_2C=CHCOOH$, 3-butenoic acid (vinylacetic acid) $H_2C=CHCH_2COOH$, 4-pentenoic acid $H_2C=CHCH_2CH_2COOH$, and other olefinic acids with carbon chains of varying length.

The Organic Amine

Some representative examples of suitable organic amines which can be used include linear alkyl diamines such as hexamethylene diamine, ethylene diamine, mixtures of such linear alkyl diamines, as well as other amines such as decamethylene diamine.

The Organic Amide

Since one step of the process of the present invention, as illustrated schematically below, involves a reaction scenario in which an olefinic acid is reacted with an organic diamine to produce the organic diamide, the particular organic diamide will necessarily depend upon the particular olefinic acid and organic diamine which are employed.

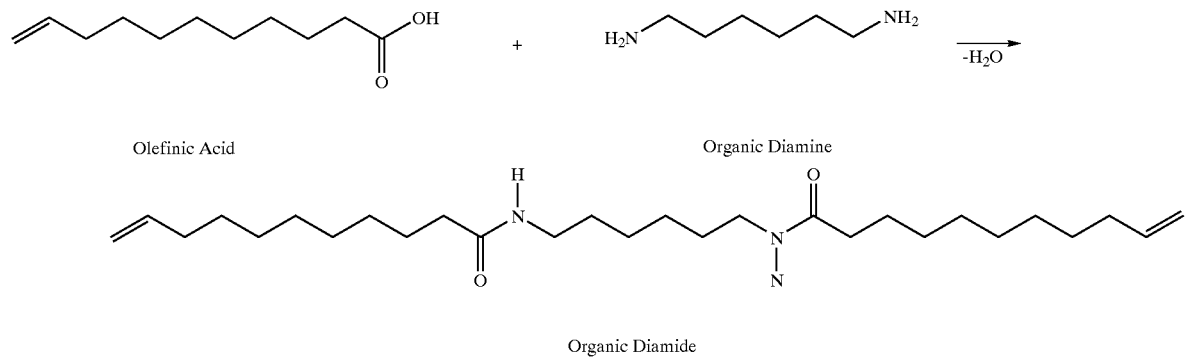

Olefinic Acid

Organic Diamine

Organic Diamide

-continued

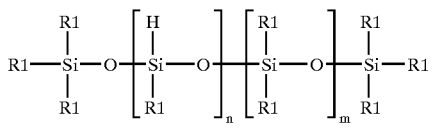

Formula II

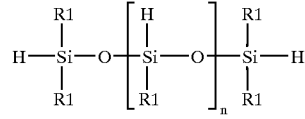

Formula III

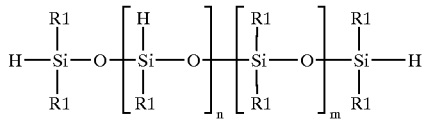

Formula IV

In these formulas, R1 represents (i) an alkyl group containing 1–20 carbon atoms such as methyl, ethyl, propyl, isopropyl, butyl, isobutyl, pentyl, hexyl, octyl, dodecyl, and octadecyl; (ii) an aryl group such as phenyl, xenyl, i.e., diphenyl, napthyl, and anthracyl; (iii) an alkaryl, i.e., alkylaryl group such as tolyl and xylyl; (iv) an aralkyl, i.e., arylalkyl group such as benzyl, i.e., phenylmethyl, phenylethyl, i.e., phenethyl, and 2-phenylpropyl; and (v) n and m each have a value of 1–1,000. The HFPOS in Formulas I–IV contains at least one pendant hydrogen.

In this regard, it should be noted that some level of saturated or non-vinyl terminated olefinic acid may be needed to limit the crosslink-density, in accordance with our copending U.S. patent application Ser. No. 10/145,311, filed May 15, 2002, entitled *Methods for Making Silicone-Organic Copolymers.*

The organic amide is then in turn reacted with the hydride-functional polyorganosiloxane in the presence of a hydrosilylation catalyst to form siloxane-based polyamide elastomers.

The Catalyst

As noted and explained above in the BACKGROUND section of the application, a catalyzed hydrosilylation reaction is employed according to this invention, and so the process requires a catalyst to effect the reaction between the hydride functional polyorganosiloxane and the material containing unsaturation, i.e., the organic diamide in the case of the present invention. Suitable catalysts are Group VIII transition metals, i.e., the noble metals. Such noble metal catalysts are described in U.S. Pat. No. 3,923,705, incorporated herein by reference to show platinum catalysts. One preferred platinum catalyst is Karstedt's catalyst, which is described in Karstedt's U.S. Pat. Nos. 3,715,334 and 3,814,730, incorporated herein by reference. Karstedt's catalyst is a platinum divinyl tetramethyl disiloxane complex typically containing about one weight percent of platinum in a solvent such as toluene. Another preferred platinum catalyst is a reaction product of chloroplatinic acid and an organosilicon compound containing terminal aliphatic unsaturation. It is described in U.S. Pat. No. 3,419,593, incorporated herein by reference. Most preferred as the catalyst is a neutralized complex of platinous chloride and divinyl tetramethyl disiloxane, for example as described in U.S. Pat. No. 5,175,325.

The noble metal catalyst can be used in an amount of from 0.00001–0.5 parts per 100 weight parts of the hydride functional polyorganosiloxane. Preferably, the catalyst should be used in an amount sufficient to provide 5–15 parts per million (ppm) Pt metal per total composition.

The Solvent

The common assignee's U.S. Pat. No. 5,811,487 (Sep. 22, 1998) and U.S. Pat. No. 5,889,108 (Mar. 30, 1999) contain extensive lists of appropriate compositions which can be used, among which are for example, (i) volatile polydimethylsiloxanes such as hexamethyldisiloxane, octamethyltrisiloxane, and decamethylcyclopentasiloxane, (ii) nonvolatile polydimethylsiloxanes having a viscosity generally in the range of 5–1,000 centistoke (mm$^2$/s), (iii) fragrances such as musk and myrrh, and (iv) mixtures thereof.

Organic oils such as natural oils derived from animal, vegetable, or mineral sources are also suitable. Most preferred are modern cosmetic oils known to be safe for cosmetic purposes such as almond oil, apricot kernel oil, avocado oil, cacao butter (theobroma oil), carrot seed oil, castor oil, citrus seed oil, coconut oil, corn oil, cottonseed oil, cucumber oil, egg oil, jojoba oil, lanolin oil, linseed oil, mineral oil, mink oil, olive oil, palm kernel oil, peach kernel oil, peanut oil, rapeseed oil, safflower oil, sesame oil, shark liver oil, soybean oil, sunflower seed oil, sweet almond oil, tallow (beef) oil, tallow (mutton) oil, turtle oil, vegetable oil, whale oil, and wheat germ oil.

Solvents considered in the art as being non-aqueous polar solvents can be used, although compositions containing such solvents intended for personal care applications, should be limited to only non-aqueous polar solvents generally recognized as being cosmetically acceptable. Some representative examples of cosmetically acceptable non-aqueous polar solvents which can be used are monohydroxy alcohols such as ethyl alcohol and isopropyl alcohol; diols and triols such as propylene glycol, 1,2-hexanediol CH$_3$(CH$_2$)$_3$CH(OH)CH$_2$OH, and glycerol; glycerol esters such as glyceryl triacetate(triacetin), glyceryl tripropionate(tripropionin), and glyceryl tributyrate (tributyrin); and polyglycols such as polyethylene glycol. In applications other than personal care, however, these and other non-aqueous polar solvents can be employed.

While the use of a solvent is beneficial in many cases, the use of one or more solvents is not absolutely required. For example, in typical state of the art siloxane-based polyamide systems, toluene and xylene have been generally used, but possess the disadvantage in that they require removal by an added stripping process when the siloxane-based polyamides are intended for applications where odor, health, and/or environmental regulations are a concern. In such instances, no solvent or the use of compositions such as decamethylcyclopentasiloxane and phenyl tris (trimethylsiloxy)silane are generally considered solutions. Similarly, polypropylene glycol ethers of linear alcohols such as myristyl alcohol, may also be used. Typical of these glycol ethers are compositions such as PPG-3 myristyl ether and PPG-4 myristyl ether.

When solvents are omitted, siloxane-based polyamides of high molecular weight with a nearly clear appearance and low color can be made, when there is sufficient mixing during polymerization. Solventless as used herein is intended to cover instances wherein (i) minor amounts of residual solvent are introduced as part of the catalyst preparation, as well as to (ii) instances wherein no additional solvent is present.

Carrying out of the process is simply a matter of combining the hydride functional polyorganosiloxane(s), the material containing unsaturation, i.e., the organic amide, and the catalyst; and mixing these ingredients. The reaction temperature can vary over a wide range, and the optimum temperature is dependent upon the concentration of the catalyst and the nature of the reactants. Ordinarily, it is best to keep the reaction temperature below about 300° C. Best results with most reactants can be obtained by initiating the reaction at about 80° C. to 180° C., and maintaining the reaction within reasonable limits of this range.

Typically, the process is carried out using approximately a 1:1 molar ratio of the hydride functionality within the polyorganosiloxane and the material containing unsaturation. It is expected that useful materials may also be prepared by carrying out the process with an excess of either the hydride functional polyorganosiloxane or the material containing unsaturation, but this would be considered a less efficient use of the materials. When the process includes the use of a solvent(s), the solvent is present in an amount of 1–85 percent by weight, based on the total weight of the composition. As previously noted, however, the solvent(s) component of the process is optional, and so it can be omitted, if desired.

EXAMPLES

The following examples are set forth in order to illustrate the invention in more detail.

The hydride functional polyorganosiloxanes used in these examples were copolymers having a structure corresponding to Formula II noted above. In Example 1, the value of m was 93 and the value of n was 6. In Example 2, the value of m was 396 and the value of n was 4.

Example 1

A 500 ml three neck round bottom flash, equipped with a temperature probe, an electrical stirrer, and a condenser, was charged with 7.6 gram of an organic diamide prepared by reacting undecylinic acid and hexamethylene diamine, 7.6 gram of PPG-4 myristyl ether (solvent), and 160 gram of decamethylcycolpentasiloxane (solvent). The mixture was heated to 130° C. for about 15 minutes to dissolve the organic diamide. About 40 gram of a hydride functional polyorganosiloxane was added dropwise via an addition funnel. Following the addition of about 5 gram of the hydride functional polyorganosiloxane, about 0.2 gram of a platinum catalyst was added. After addition of the remaining siloxane(s), another 0.2 gram of platinum catalyst was added. The reaction mixture was stirred for about 1 hour to allow growth and crosslinking of the polymer. Analysis of the final composition indicated that it was a gel-like material with an elastomeric portion having a molecular weight of about 107, 500. The polydispersity of this elastomer was 3.66.

Example 2

A 500 ml three neck round bottom flash, equipped with a temperature probe, an electrical stirrer, and a condenser, was charged with 6.35 gram of an organic diamide prepared by reacting undecylinic acid and hexamethylene diamine, 3.24 gram of PPG-4 myristyl ether(solvent), and 52 gram of decamethylcycolpentasiloxane (solvent). The mixture was heated to 130° C. for about 15 minutes to dissolve the organic diamide. About 212 gram of a hydride functional polyorganosiloxane was added dropwise via an addition funnel. Following the addition of about 5 gram of the hydride functional polyorganosiloxane, about 0.2 gram of a platinum catalyst was added. After addition of the remaining siloxane(s), another 0.2 gram of the platinum catalyst was added. The reaction mixture was stirred for about 1 hour to allow growth and crosslinking of the polymer. Analysis of the final composition indicated that it was a gel-like material with an elastomeric portion having a molecular weight of about 151,000. The polydispersity of this elastomer was 3.05.

The siloxane-based polyamide elastomer according to this invention is especially useful in personal care, for example, in the preparation of antiperspirants and deodorants. It can be used in skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers. It can be used in hair shampoos, hair conditioners, hair sprays, mousses, permanents, depilatories, and cuticle coats. In cosmetics, it can be added to make-ups, color cosmetics, foundations, blushes, lipsticks, eyeliners, mascara, oil removers, color cosmetic removers, and powders. In such applications, it may include oil soluble, polar solvent soluble, and water soluble ingredients such as vitamins.

The siloxane-based polyamide elastomer is also capable of functioning as a carrier for pharmaceuticals, biocides, herbicides, pesticides, and other biologically active substances; and it has utility as an additive for cellulosic or synthetic nonwoven carrier substrates used in wet-like cleansing wipes such as wet-wipes, tissues, and towels, marketed generally for personal hygiene and household cleaning tasks. The siloxane-based polyamide elastomer can also be used to modify thermoplastic nylons, and for treating woven and non-woven textiles such as air bags, carpeting, and apparel Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A method of making a siloxane-based polyamide elastomer comprising heating and reacting an organic amide with a hydride functional polyorganosiloxane in the presence of a hydrosilylation catalyst to form the siloxane-based polyamide elastomer; the hydride functional polyorganosiloxane being a polymer or copolymer having a formula selected from the group consisting of

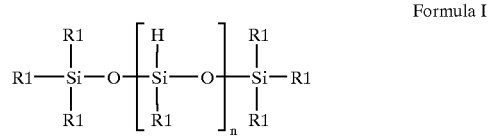

Formula I

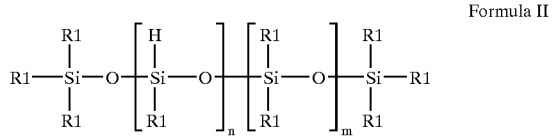

Formula II

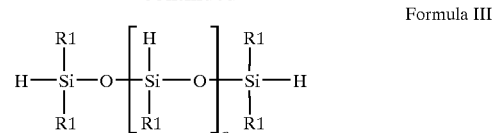

Formula III

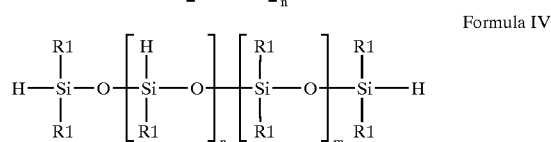

Formula IV wherein R1 represents (i) an alkyl group containing 1–20 carbon atoms; (ii) an aryl group; (iii) an alkaryl group; or (iv) an aralkyl group; and (v) n and m each have a value of 1–1,000.

2. A method according to claim 1 in which the organic amide is a diamide prepared from an organic diamine selected from the group consisting of hexamethylene diamine, ethylene diamine, and decamethylene diamine, and an olefinic acid.

3. A method according to claim 2 in which the olefinic acid is a compound selected from the group consisting of undecylenic acid, acrylic acid, 3-butenoic acid, and 4-pentenoic acid.

4. A siloxane-based polyamide elastomer prepared according to the method defined in claim 2.

5. A product containing the siloxane-based polyamide elastomer of claim 4 in which the product is selected from the group consisting of antiperspirants, deodorants, skin creams, skin care lotions, moisturizers, facial treatments, acne removers, wrinkle removers, personal cleansers, facial cleansers, bath oils, perfumes, colognes, sachets, sunscreens, pre-shave lotions, after-shave lotions, shaving soaps, shaving lathers, hair shampoos, hair conditioners, hair sprays, mousses, permanents, depilatories, cuticle coats, make-up, color cosmetics, foundations, blushes, lipsticks, eyeliners, mascara, oil removers, color cosmetic removers, bath powders, body powders, pharmaceuticals, biocides, herbicides, pesticides, biologically active substances, cellulosic substrates, synthetic nonwoven substrates, wet-cleansing wipes tissues, and towels.

6. A method of treating hair, skin, or underarm, comprising applying to hair, skin, or underarm the siloxane-based polyamide elastomer of claim 4.

7. A method of modifying thermoplastic nylons comprising applying to the thermoplastic nylons the siloxane-based polyamide elastomer of claim 4.

8. A method of treating woven and non-woven textiles comprising applying to textiles the siloxane-based polyamide elastomer of claim 4.

9. A method of making a siloxane-based polyamide elastomer comprising heating and reacting (i) an organic amide with (ii) a hydride functional polyorganosiloxane, in the presence of (iii) a solvent, and (iv) a hydrosilylation catalyst, to form the siloxane-based polyamide elastomer; the hydride functional polyorganosiloxane being a polymer or copolymer having a formula selected from the group consisting of

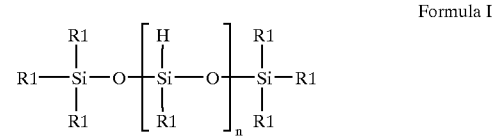

Formula I

-continued

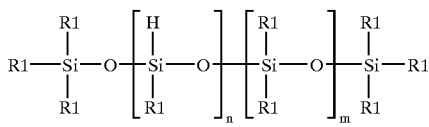
Formula II

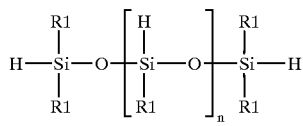
Formula III

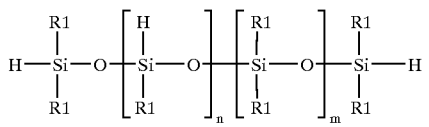
Formula IV wherein R1 represents (i) an alkyl group containing 1–20 carbon atoms; (ii) an aryl group; (iii) an alkaryl group; or (iv) an aralkyl group; and (v) n and m each have a value of 1–1,000.

10. A method according to claim 9 in which the organic amide is a diamide prepared from an organic diamine selected from the group consisting of hexamethylene diamine, ethylene diamine, and decamethylene diamine, and an olefinic acid.

11. A method according to claim 10 in which the olefinic acid is a compound selected from the group consisting of undecylenic acid, acrylic acid, 3-butenoic acid, and 4-pentenoic acid.

12. A siloxane-based polyamide elastomer prepared according to the method defined in claim 10.

13. A product containing the siloxane-based polyamide elastomer of claim 12 in which the product is selected from the group consisting of antiperspirants, deodorants, skin creams, care lotions, moisturizers, facial treatments, acne removers, wrinkle removers, personal cleansers, facial cleansers, bath oils, perfumes, colognes, sachets, sunscreens, pre-shave lotions, after-shave lotions, shaving soaps, shaving lathers, hair shampoos, hair conditioners, hair sprays, mousses, permanents, depilatories, cuticle coats, make-up, color cosmetics, foundations, blushes, lipsticks, eyeliners, mascara, oil removers, color cosmetic removers, bath powders, body powders, pharmaceuticals, biocides, herbicides, pesticides, biologically active substances, cellulosic substrates, synthetic nonwoven substrates, wet-cleansing wipes, tissues, and towels.

14. A method of treating hair, skin, or underarm, comprising applying to hair, skin, or underarm the siloxane-based polyamide elastomer of claim 12.

15. A method of modifying thermoplastic nylons comprising applying to the thermoplastic nylons the siloxane-based polyamide elastomer of claim 12.

16. A method of treating woven and non-woven textiles comprising applying to the textiles the siloxane-based polyamide elastomer of claim 12.

* * * * *